(12) United States Patent
Oroskar et al.

US009556116B2

(10) Patent No.: US 9,556,116 B2
(45) Date of Patent: Jan. 31, 2017

(54) KRILL OIL REFINERY FOR PURIFICATION OF KRILL OIL EXTRACT

(71) Applicant: Orochem Technologies, Inc., Naperville, IL (US)

(72) Inventors: Anil R. Oroskar, Oak Brook, IL (US); Asha A. Oroskar, Oak Brook, IL (US); Alexander B. Smetana, Park Ridge, IL (US); Slobodan Milasinovic, Chicago, IL (US); Xuejun Zang, Fox Pointe, WI (US)

(73) Assignee: OROCHEM Technologies, Inc., Naperville, IL (US)

( * ) Notice: Subject to any disclaimer, the term of this patent is extended or adjusted under 35 U.S.C. 154(b) by 0 days.

(21) Appl. No.: 14/619,102

(22) Filed: Feb. 11, 2015

(65) Prior Publication Data

US 2016/0229781 A1 Aug. 11, 2016

(51) Int. Cl.
| | | |
|---|---|---|
| C07C 45/85 | (2006.01) | |
| C07C 403/24 | (2006.01) | |
| C11B 3/00 | (2006.01) | |
| C11B 3/10 | (2006.01) | |

(52) U.S. Cl.
CPC ............. *C07C 403/24* (2013.01); *C11B 3/001* (2013.01); *C11B 3/006* (2013.01); *C11B 3/008* (2013.01); *C11B 3/10* (2013.01); *C07C 2101/16* (2013.01)

(58) Field of Classification Search
CPC ........................... B01D 15/1828; C07C 45/85
See application file for complete search history.

(56) References Cited

U.S. PATENT DOCUMENTS

| | | | | |
|---|---|---|---|---|
| 2,669,713 | A | * | 2/1954 | Osmun ................ B01J 49/0073 210/670 |
| 2,985,589 | A | | 5/1961 | Broughton |
| 7,473,801 | B2 | | 1/2009 | Takamatsu |
| 8,772,516 | B2 | | 7/2014 | Katevas |
| 2003/0054084 | A1 | | 3/2003 | Hruschka |
| 2008/0045746 | A1 | | 2/2008 | Takamatsu |
| 2009/0227678 | A1 | | 9/2009 | Bijl |
| 2014/0065236 | A1 | | 3/2014 | Sclabos Katevas |
| 2014/0100380 | A1 | | 4/2014 | Bijl |
| 2014/0107072 | A1 | | 4/2014 | Tilseth |
| 2014/0370115 | A1 | | 12/2014 | Hoem |

FOREIGN PATENT DOCUMENTS

| | | |
|---|---|---|
| CN | 103602517 A * | 2/2014 |
| WO | 2009132463 | 11/2009 |

OTHER PUBLICATIONS

Machine translation for CN 103602517 A, Feb. 26, 2014.*
Ellingsen et al. Journal of Chemical Ecology, vol. 12, No. 1, 1986, 155-168.*
Trotter et al. Pharmaceutical Technology, 2002 p. 60-70.*
Soni, Madhu, "Krill Oil GRAS Notification—SUPERBA™ Krill Oil extracted from Antarctic krill, Euphausia superba", (Submitted to US Food and Drug Administration, Dec. 2010) (http://www.fda.gov/ucm/groups/fdagov-public/@fdagov-foods-gen/documents/document/ucm274421.pdf).
Hoem, Nils, "Composition of Antarctic krill oil and methods for its harvesting, production and qualitative and quantitative analysis",Aker BioMarine, Newcastle Australia, Nov. 2013.
Anonymous, "Krill oil quality and freshness indicators", Enzymotec Delivering Lipids Brochure, Dec. 2010.
Yuan, Jianping, "Characteristics and chromatographic separation of astaxanthin and its esters from the microalga haematococcus pluvialis", The University of Hong Kong, China (1999) (http://hdl.handle.net/10722/35452).
International Search Report for corresponding International Application PCT/US2016/017343 mailed May 20, 2016.
Written Opinion for corresponding International Application PCT/US2016/017343 mailed May 20, 2016.

* cited by examiner

*Primary Examiner* — Yong Chu
*Assistant Examiner* — Ana Z Muresan
(74) *Attorney, Agent, or Firm* — Richard P. Silverman & Assoc., LLC

(57) ABSTRACT

Disclosed is a chromatographic process complex for the refining of krill oil extract including desalting, removal of impurities such as trimethylamine oxide (TMAO), and the production of krill oil products including desalted krill oil extract, polar lipid products having polar lipid contents greater than 50 wt-% on a dry or solvent free basis, neutral lipid streams for biodiesel production and astaxanthin. The refinery includes a continuous desalting zone, a fixed bed polar lipid extraction zone to adsorb neutral lipids and astaxanthin to provide a polar lipid extract stream comprising solvent and polar lipids and being essentially free of neutral lipids and astaxanthin, and an astaxanthin separation zone to recover essentially pure astaxanthin and provide a neutral lipid stream. The enriched products of the krill oil refinery are essentially free of TMAO and salt and provide products which can be used as dietary supplements and as medicinal additives.

13 Claims, 9 Drawing Sheets

KRILL OIL REFINERY FOR PURIFICATION OF KRILL OIL EXTRACT

FIELD OF THE INVENTION

This invention concerns generally with methods for desalting and recovery of purified components of krill oil extract. More particularly, the invention relates to a series of separation processes based on adsorption and chromatographic separation to remove salts and trimethylamine N-oxide (TMAO) from the krill oil extract, and recover products comprising neutral lipids, polar lipids, and astaxanthin. Most particularly, the invention relates to a desalting process based on cationic and anionic adsorption in a continuous simulated moving process to remove salts and trimethylamine N-oxide from krill oil extract, and a series of fixed bed extraction steps to recover products comprising desalted krill oil, neutral lipids, polar lipids, and astaxanthin.

BACKGROUND

Krill is a small crustacean which lives in all the major oceans world-wide. Krill can be found in the Pacific Ocean (*Euphausia pacifica*), in the Northern Atlantic (*Meganyctiphanes norvegica*) and in the Southern Ocean off the coast of Antarctica (*Euphausia superba*). Krill is a key species in the ocean as it is the food source for many animals such as fish, birds, sharks and whales. Krill can be found in large quantities in the ocean and the total biomass of Antarctic krill (*E. superba*) is estimated to be in the range of 300-500 million metric tons.

Krill has developed an efficient enzymatic digestive apparatus resulting in a rapid breakdown of the proteins into amino acids. Therefore, in order to prevent the degradation of krill the enzymatic activity is either reduced by storing the krill at low temperatures or the krill is made into a krill meal. During the krill meal process the krill is cooked so that all the active enzymes are denatured in order to eliminate all enzymatic activity. Krill is rich in phospholipids which act as emulsifiers. Thus, it is more difficult to use mechanical separation methods to separate water, fat, and proteins from krill oil, than it is in a regular fish meal production line. In addition, krill becomes solid, gains weight and loses liquid more easily when mixed with hot water. Eventually this may lead to a gradual build-up of coagulated krill proteins in the cooker and a non-continuous operation due to severe clogging problems. In order to alleviate this, hot steam must be added directly into the cooker. This operation is energy demanding and may also result in a degradation of unstable bioactive components in the krill such as omega-3 fatty acids, phospholipids and astaxanthin.

Traditional krill meal processing on board, in some factory vessels, produces only a small amount of krill oil. This krill oil is usually enriched in neutral lipids with very low or undetectable amount of phospholipids (0.5%). Normally, during the traditional on board krill process, fresh krill is heated using an indirect heating cooker with rotating screw conveyor, followed by a twin-screw press and drier. The press liquid obtained by the twin-screw press is passed through a decanter to remove the insoluble solids. The clarified decanter liquid is then used to feed separators centrifuges to separate the krill oil normally enriched with neutral lipids and astaxanthin. In this traditional process the phospholipids are bound to the proteins in the press cake, or krill meal.

US Patent Application Publication No. 20140107072 (which is hereby incorporated by reference) discloses a method for making krill meal using a two-step cooking process. In the first step the proteins and phospholipids are removed from the krill and precipitated as a coagulum. In the second stage the krill without phospholipids are cooked. Following this, residual fat and astaxanthin are removed from the krill using mechanical separation methods.

Typically, krill oil contains salt and trimethylamine N-oxide (TMAO), a natural and nontoxic substance. High TMAO levels in polar fishes and crustaceans are thought to increase osmotic concentration, thus depressing the freezing point of the body fluids. Odor is one of the most important parameters used to evaluate fish and fish oil freshness. Volatile amines such as ammonia and TMA, a degradation product of TMAO, are the characteristic molecules responsible for the fishy odor and flavor present in fish oils. Thus, TMAO is a precursor to TMA and as such must be removed from krill oil or krill oil extract to maintain the krill oil as an acceptable product which is fit for human consumption.

US Patent Application Publication No. 20140065236 discloses a solvent free process for obtaining phospholipids and neutral lipids enriched krill oils containing DHA and EPA poly-unsaturated fatty acids and astaxanthin. The process includes cooking fresh krill at high temperature-without agitation and or grinding; decanting the cooked krill for obtaining a partial de-fatted and de-watered solid and a liquid; squeezing the obtained solid to obtain a press liquid and a solid fraction; centrifuging the press liquid to obtain the phospholipids enriched krill oil; centrifuging of the decanter liquid obtained to obtain the neutral lipid enriched krill oil and stick water. Stick water is a viscous quickly decomposing, and evil-smelling liquor that is obtained as a by-product in the wet process of manufacturing krill meal and krill oil by cooking the krill with steam and pressing and that is often concentrated by evaporation for use in animal feeds as a source of vitamins and amino acids.

Krill meal is a biomass composed of lipids, carbohydrates, and proteins. The krill meal is extracted in a solvent extraction process typically using ethanol as a solvent to remove proteins and free carbohydrates to provide a krill oil extract. The solvent used is typically food-grade quality. Following solvent extraction, the defatted krill meal and the ethanol oil solution are separated by physical means such as filtration or centrifugation. The recovered krill oil extract comprises neutral lipids, polar lipids, and astaxanthin.

Current production of high phospholipid krill oil is exemplified by the Aker BioMarine process. The Antarctic krill used in the production of SUPERBA Krill Oil (Available from Aker BioMarine AS, Oslo, NO) are naturally occurring organisms harvested in the wild. The harvested Antarctic krill is cooked and dried on the vessel to prepare krill meal. The krill meal is subjected to a solvent extraction process with ethanol as the solvent to remove proteins and free carbohydrates and provide an ethanol oil solution comprising the extracted oil and ethanol. Following extraction, the defatted krill meal and the ethanol oil solution are separated in a conventional manner. The ethanol-oil solution is then concentrated by evaporation. The ethanol-oil solution comprises ethanol, neutral and polar lipids, and astaxanthin. The ethanol-oil solution is clarified by centrifugation and the clarified ethanol solution is evaporated to provide a krill oil product. See "Krill Oil GRAS Notification-SUPERBA™ Krill Oil extracted from Antarctic krill, *Euphausia superba*", (Submitted to US Food and Drug Administration, December 2010).

Krill oil and krill oil extract produced in the manner described hereinabove does not recover high yields or high purity of astaxanthin and the high phospholipid krill oil produced is only a portion of the phospholipids in the krill meal. Methods are sought to improve the recovery of high phospholipid krill oil, krill oil components, and astaxanthin without subjecting the oils to chemical and physical conditions which would result in degradation and which can reduce the overall recovery of these valuable components.

SUMMARY OF THE INVENTION

In one embodiment, the present invention is a process for refining of krill oil extract into higher value products, said process comprising:
a) passing a krill oil extract comprising polar lipids, neutral lipids, trimethylamine oxide (TMAO), salt and astaxanthin and an effective amount of solvent to dilute the krill oil extract to a concentration of between about 2 and about 7 wt-% on a dry basis in the solvent, the solvent being a mixture of ethanol and water having an ethanol to water ratio of from about 99:1 to about 95:5 to provide a desalter feed stream;
b) introducing the desalter feed stream to at least one of a plurality of desalting stages in a krill oil simulated moving bed desalting zone, each desalting stage comprising a first column containing a cation exchange resin having a top and a bottom and a second column containing an anion exchange resin having a top and a bottom, and the bottom of the first column being in fluid communication with the top of the second column, wherein at least a portion of the desalting stages are active desalting stages, and at least one desalting stage is undergoing desalting regeneration and withdrawing from one or more active desalting stage a desalted lipid rich stream being essentially free of TMAO and salt;
c) introducing at least a portion of the desalted lipid rich stream to a polar liquid extraction zone comprising a fixed bed adsorber containing a macroporous styrenic polymeric bead type resin effective to adsorb neutral lipids and provide a polar lipid extract stream comprising solvent and at least 50 wt-% polar lipids on a dry basis, and intermittently regenerating the fixed bed adsorber with a hot ethanol stream at a hot regeneration temperature between about 40° C. and about 60° C. to provide a neutral lipid raffinate stream comprising solvent, neutral lipids and astaxanthin;
d) introducing all or at least a portion of the neutral lipid raffinate stream to an astaxanthin extraction zone and therein contacting a steam activated carbon adsorbent to adsorb astaxanthin and provide a neutral lipid rich stream comprising solvent and neutral lipids, and regenerating the steam activated carbon with anisole to desorb the astaxanthin to provide an astaxanthin rich stream comprising anisole and astaxanthin;
e) recovering solvent from at least a portion of the desalted lipid rich stream to provide a desalted krill oil extract product;
f) recovering solvent from the neutral lipid rich stream to provide a neutral lipid product stream;
g) recovering solvent from the polar lipid extract stream, to provide a polar lipid product having a PL content greater than 50 wt-% on a dry basis; and,
recovering anisole from the astaxanthin product stream to provide a high purity astaxanthin product.

In a further embodiment, the present invention is process for desalting a krill oil extract stream, the krill oil extract stream comprising neutral lipids, polar lipids, astaxanthin, salts and trimethylamine N-oxide (TMAO) to provide a desalted crude krill oil product, a refined polar lipid product, an astaxanthin product, and a reject stream comprising neutral lipids, the process comprising:

a) diluting the krill oil extract stream to a desalter concentration of between about 4 and about 7 percent by weight in a polar solvent comprising ethanol and water having an ethanol:water ratio of between of about 95:5 to 99:1 to provide a diluted krill oil stream;
b) passing the diluted krill oil stream to a filtration zone having a 0.45 micron filter to provide a filtered desalter feed stream;
c) passing the filtered desalter feed stream to at least one active desalting stage in a desalting zone having a plurality of desalting stages comprising at least two active desalting stages and at least one regenerating desalting stage, each desalting stage comprising a cation column containing a cation adsorbent in serial fluid communication with an anion column containing an anion adsorbent to adsorb the salt and the TMAO, the cation column and the anion column having a top and a bottom, the desalting process comprising:
   i. distributing the filtered desalter feed stream to the active desalting stages, one active desalting stage being in a lead position and one active being in a terminal position and operating in parallel such that a portion of the filtered feed stream is passed to the top of each cation column and a portion of the desalted effluent stream is withdrawn from the bottom of each anion column of each of the two active desalting stages and collecting the portion of the desalted effluent stream from the active desalting stages to provide a first desalted krill oil stream;
   ii. regenerating the regenerating desalting stage consisting of a regen cation column and a regen anion column according to a regeneration cycle comprising:
   (a) flushing the regenerating desalting stage with a mobile phase solvent having a ratio of 95:5 parts ethanol to water to a ratio of 99:1 parts ethanol to water to recover desalted lipids in a second desalted krill oil stream;
   (b) washing the regenerating desalting stage with a water wash stream comprising water to provide a first waste stream;
   (c) reactivating the regen cation column by passing an acid stream comprising an aqueous hydrochloric acid solution comprising about 2 to about a 6 wt-% hydrochloric acid to the regen cation column to provide a reactivated regen cation column and withdrawing a second waste stream;
   (d) reactivating the regen anion column by passing an aqueous basic solution comprising about 5 to about 8 wt-% sodium carbonate to the regen anion column to provide a reactivated regen anion column and withdrawing a third waste stream;
   (e) separately washing the regen cation column and regen anion column with a water wash stream comprising water to remove excess ions and to provide a washed reactivated desalting stage and withdrawing a fourth waste stream; and,
   (f) passing the mobile phase solvent having a ratio of 95:5 parts ethanol to water to a ratio of 99:1 parts ethanol to water to recondition the reactivated desalting stage to provide a newly regenerated desalting stage;
d) cycling the desalting zone by intermittently terminating distributing the filtered desalter feed stream to the active desalting stages and shifting or exchanging the newly regenerated desalting stage for the active desalting stage in the lead position and shifting the active desalting in the terminal position to become the regenerating desalting stage;
e) combining at least a portion of the first desalted krill oil stream and the second desalted krill oil stream and passing the desalted admixture to a first solvent recovery zone to remove solvent in a first solvent stream and to provide a first krill oil product stream comprising neutral lipids, polar lipids and astaxanthin;

f) passing a portion of the first desalted stream comprising neutral lipids, polar lipids, astaxanthin and solvent to a fixed bed extraction zone containing a macroporous styrenic polymeric bead type resin to adsorb neutral lipids and astaxanthin to provide a polar lipid extract stream comprising solvent and polar lipids and being essentially free of neutral lipids and astaxanthin, and on regeneration with a second mobile phase solvent providing a fixed bed raffinate stream comprising the second mobile phase solvent, neutral lipids, and astaxanthin;

g) passing the polar lipid extract stream to a second solvent recovery zone to recover solvent in a second solvent stream and to provide a high purity polar lipid product stream having a purity of greater than or equal to 90 wt-% polar lipids on a solvent free basis;

h) passing the fixed bed raffinate stream to an astaxanthin separation zone and therein contacting the fixed bed raffinate stream with a selective adsorbent comprising activated carbon to adsorb astaxanthin and to provide a second raffinate stream comprising neutral lipids and solvent and regenerating the astaxanthin separation zone with a third desorbent comprising anisole to provide an astaxanthin stream comprising the third desorbent and astaxanthin;

i) separating the astaxanthin stream in a fourth solvent recovery zone to provide an astaxanthin product stream and a recovered anisole stream and returning at least a portion of the recovered anisole stream to the astaxanthin separation zone; and, j) admixing a portion of the first krill oil product stream and the polar lipid extract stream to provide at least one refined polar lipid product having a polar lipid content between about 40 and 99 wt-% polar lipids on a solvent free basis.

In a still further embodiment, the invention is a process for desalting a krill oil extract stream, said process comprising:

a) diluting the krill oil extract stream comprising polar lipids, neutral lipids, TMAO, salts, and astaxanthin to a desalter concentration of about 5 percent by weight in a polar solvent comprising ethanol and water having an ethanol:water ratio of between of about 95:5 to 99:1 to provide a diluted krill oil stream;

b) passing the diluted krill oil stream to a filtration zone having a 0.45 micron filter to provide a filtered desalter feed stream;

c) passing the filtered desalter feed stream to at least one active desalting stage in a desalting zone having a plurality of desalting stages comprising at least two active desalting stages and at least one regenerating desalting stage, each desalting stage comprising a cation column containing a cation adsorbent in serial fluid communication with an anion column containing an anion adsorbent to adsorb the salt and the TMAO, the cation column and the anion column having a top and a bottom, the desalting process comprising:

i. distributing the filtered desalter feed stream to the active desalting stages, one active desalting stage being in a lead position and one active being in a terminal position and operating in parallel such that a portion of the filtered feed stream is passed to the top of each cation column and a portion of the desalted effluent stream is withdrawn from the bottom of each anion column of each of the two active desalting stages and collecting the portion of the desalted effluent stream from the active desalting stages to provide a first desalted krill oil stream;

ii. regenerating the regenerating desalting stage consisting of a regen cation column and a regen anion column according to a regeneration cycle comprising:

(a) flushing the regenerating desalting stage with a mobile phase solvent having a ratio of 95:5 parts ethanol to water to a ratio of 99:1 parts ethanol to water to recover desalted lipids in a second desalted krill oil stream;

(b) washing the regenerating desalting stage with a water wash stream comprising water to provide a first waste stream;

(c) reactivating the regen cation column by passing an acid stream comprising an aqueous hydrochloric acid solution comprising about 2 to about a 6 wt-% hydrochloric acid to the regen cation column to provide a reactivated regen cation column and withdrawing a second waste stream;

(d) reactivating the regen anion column by passing an aqueous basic solution comprising about 5 to about 8 wt-% sodium carbonate to the regen anion column to provide a reactivated regen anion column and withdrawing a third waste stream;

(e) separately washing the regen cation column and regen anion column with a water wash stream comprising water to remove excess ions and to provide a washed reactivated desalting stage and withdrawing a fourth waste stream; and, (f) passing the mobile phase solvent having a ratio of 95:5 parts ethanol to water to a ratio of 99:1 parts ethanol to water to recondition the reactivated desalting stage to provide a newly regenerated desalting stage;

d) cycling the desalting zone by intermittently terminating distributing the filtered desalter feed stream to the active desalting stages and shifting or exchanging the newly regenerated desalting stage for the active desalting stage in the lead position and shifting the active desalting in the terminal position to become the regenerating desalting stage.

In another embodiment, the invention is a process for separating polar lipids from a mixture of polar lipids, neutral lipids and astaxanthin, said process comprising:

a) diluting the mixture in a solvent comprising ethanol and water having an ethanol:water ratio of between of about 95:5 to 99:1 to concentration of about 5 percent by weight of said mixture to provide a diluted mixture;

b) passing the diluted mixture to a fixed bed extraction zone containing a macroporous styrenic polymeric bead type resin to adsorb neutral lipids and astaxanthin to provide a polar lipid extract stream comprising solvent and polar lipids and being essentially free of neutral lipids and astaxanthin, and on regeneration with a second mobile phase solvent providing a fixed bed raffinate stream comprising the second mobile phase solvent, neutral lipids, and astaxanthin; and c) passing the polar lipid extract stream to a solvent recovery zone to recover solvent in a solvent stream and to provide a high purity polar lipid product stream having a purity of greater than or equal to 50 wt-% polar lipids on a solvent free basis.

In another further embodiment, the invention is a process for separating astaxanthin from a mixture comprising neutral lipids and astaxanthin, said process comprising;

a) diluting the mixture in a solvent comprising ethanol and water having an ethanol:water ratio of between of about 95:5 to 99:1 to concentration of about 5 percent by weight of said mixture to provide a diluted astaxanthin mixture;

b) introducing the diluted astaxanthin mixture to an astaxanthin extraction zone and therein contacting a steam activated carbon adsorbent to adsorb astaxanthin and to provide a neutral lipid rich stream comprising solvent and neutral lipids, c) regenerating the steam activated carbon with anisole to desorb the astaxanthin to provide an astaxanthin rich stream comprising anisole and astaxanthin;

d) recovering the anisole from the astaxanthin rich stream to provide an astaxanthin product; and, e) returning at least a portion of the anisole to step (c).

DESCRIPTION OF THE INVENTION

Typical krill Oil feed stocks for use with the krill oil refinery of the present invention include: SUPERBA Krill Oil (Available from Aker BioMarine AS, Oslo, NO), Krill Oil Extract prepared by solvent extraction of Krill Meal with an ethanol/water solvent, and other sources of krill oil. Typically krill oil comprises about 28.6 wt-% polar lipids (Phospholipids), 66.6 wt-% neutral lipids, 3.5 wt-% salt, 1.2 wt-% trimethylamine oxide (TMAO), and 0.1 wt-% astaxanthin (1000 ppm wt). The polar lipids typically are phospholipids and include the following lipids:

| | Phospholipids | |
|---|---|---|
| Symbol | Name | Mol-% |
| PC | Phosphatidylcholine | 77 |
| LPC | Lyso-Phosphatidylcholine | 15 |
| PE | Phosphatidylethanolamine | 5.8 |
| LPE | Lyso-Phosphatidylethanolamine | 1.4 |
| Other PL | Miscellaneous | 0.7 |

Figure 7:
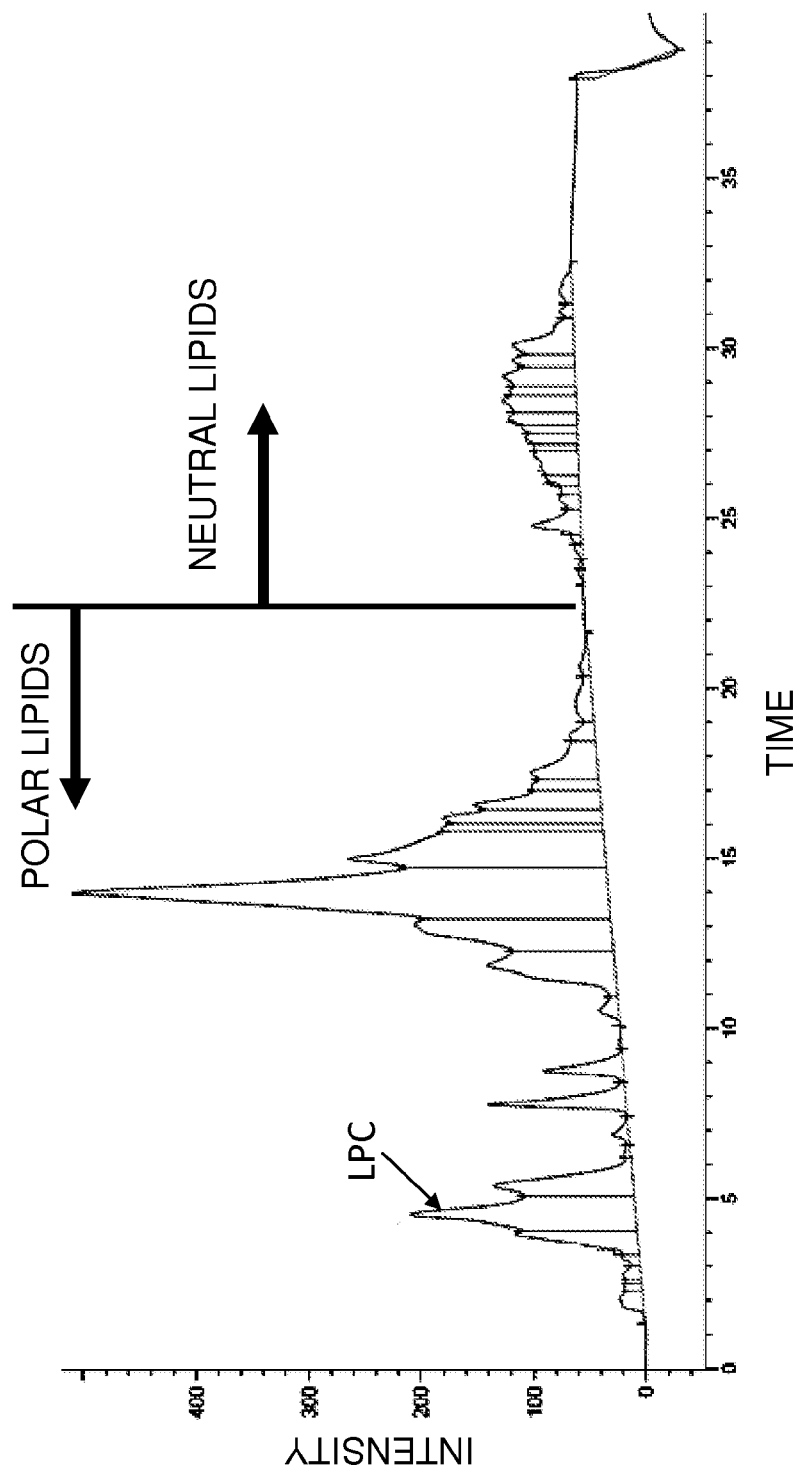
FIG. 7 is an HPLC chromatogram of the desalted krill oil feed to the fixed bed extraction zone for extraction of polar lipids.
Figure 8:
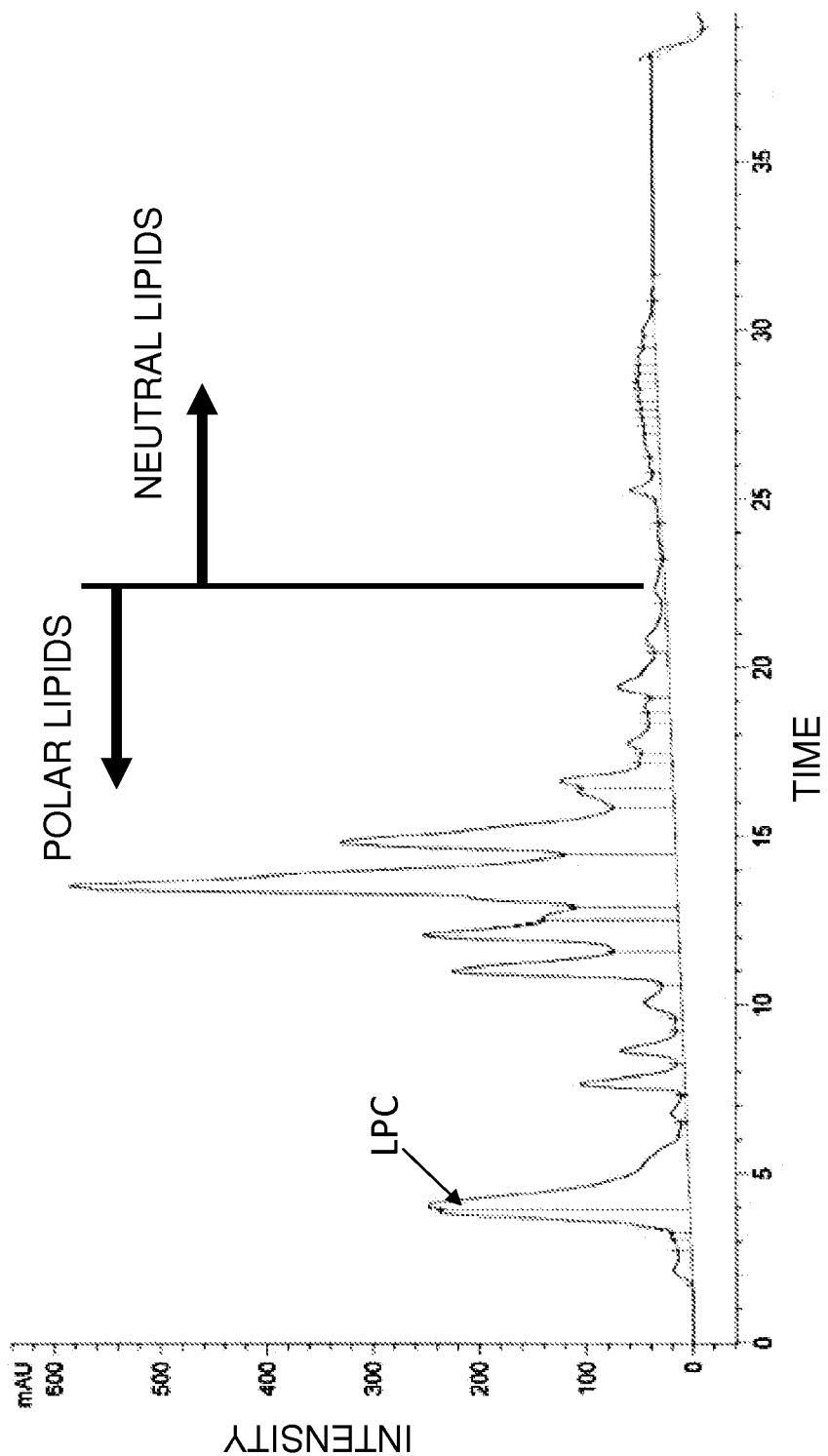
FIG. 8 is an HPLC chromatogram of the extract from the fixed bed extraction zone having a reduced amount of neutral lipids.

LPC, or Lyso-Phosphatidylcholine, is a polar lipid, but it is required to remove LPC from the krill oil extract so that it does not appear in any of the polar lipid products derived from desalted krill oil. The permissible concentration of LPC in polar liquid products is required to be less than or equal to 1 wt-% as determined by NMR analysis of the polar liquid product. It was observed that the concentration of LPC increased slightly during the krill oil desalting process of the present invention and resulted in a desalted krill oil which had a greater concentration of LPC than in the krill oil extract feed. It was surprisingly discovered that by subjecting the desalted krill oil to a fixed bed process for separating the polar lipids from the neutral lipids over a macroporous styrenic polymeric bead resin(described hereinbelow), that the LPC appeared in the first bed volume of eluate withdrawn from the fixed bed. FIG. 7 is an HPLC chromatogram of the desalted krill oil showing the first major peak to elute is the LPC peak. FIG. 8 is an HPLC chromatogram of the combined volumes collected as the extract from the fixed bed process. The LPC peak appeared in the first bed volume of the extract produced. By isolating and removing this first bed volume of eluate, it was possible to exclude LPC from the polar liquid products, and, if required, could provide an LPC rich product stream, while also providing a polar lipid extract product which was essentially free of LPC.

The neutral lipids are typically composed of long chain fatty acids attached to a glycerol back bone. A typical neutral lipid fraction derived from krill oil comprises the following fatty acid profile:

| | Neutral Lipids | |
|---|---|---|
| Symbol | Fatty Acid Species | % w/w in crude oil |
| EPA | Eicosapentaenoic Acid | 14 |
| DHA | Docosahexaenoic Acid | 8 |
| PAL | Palmitic Acid | 13 |

Salt in the krill oil is primarily sodium chloride. TMAO in krill oil is a degradation product which has an objectionable odor, and when present results in the spoilage of the krill oil product.

Conventionally extracted krill oil extract contains a maximum amount of polar lipids of about 40 wt-%, typically called PL40. Applicant's invention provides an economic route to producing krill oil products greater than 50 wt-% polar lipids, for example: from about 60 wt-% polar lipids to about 100 wt-% polar lipids. Intermediate grades of krill oil having polar lipid concentrations between 50 and 100 wt-% can be obtained by producing the 100 wt-% polar lipid product and blending it with a desired amount of desalted krill oil to achieve any intermediate polar lipid content quality grade such as 60, 65, 70, 75, 80, 85, and 90 wt-% PL on a dry basis.

The process of the present invention requires the dilution of the input or feed streams to the individual separation zones. For example, the crude krill oil or krill oil extract is diluted with a solvent comprising an alcohol such as ethanol or an ethanol/water mixture having an ethanol/water ratio of between about 95:5 and about 99:1 (vol/vol). Preferably, the solvent comprises an ethanol/water ratio of about 98:2 (vol/vol). When the feed to a simulated moving bed separation process or a fixed bed chromatographic separation process of the present invention, the effluents from that process will generally comprise the solvent. In the present invention all of the extracts and the raffinate streams can be characterized as being "rich" in a particular component, such as polar lipids, neutral lipids, or astaxanthin, and will require the further step of solvent removal. Because the polar lipids, neutral lipids and astaxanthin are temperature sensitive, the solvent removal steps will require low temperature evaporation or vacuum distillation (from room temperature to about less than or equal to about 40° C.) to affect the solvent removal. Because different components such as TMAO or astaxanthin may be present in the "rich" streams, it may be economical to separate or group the solvent removal steps to avoid contaminating the solvent with an odor or a color at particular points in the process.

DESCRIPTION OF THE DRAWINGS

Figure 1:
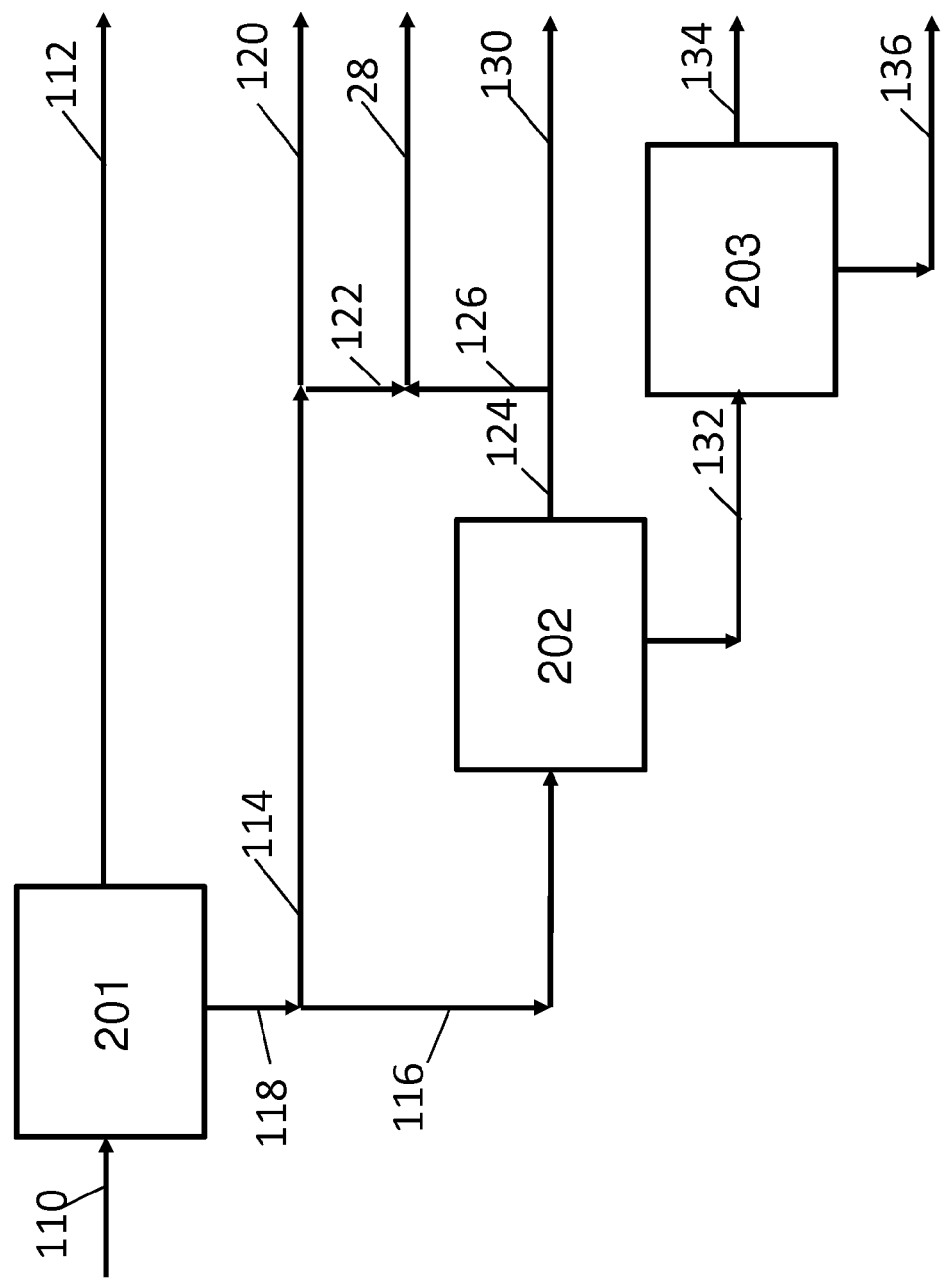
FIG. 1 is a schematic block flow diagram illustration of one embodiment of an overall flow scheme of a krill oil refinery.

FIG. 1, illustrates one embodiment of an overall simplified flow scheme of a krill oil refinery. With reference to FIG. 1, a crude krill oil, or krill oil extract stream in line 10 comprising neutral lipids, polar lipids, salts, trimethylamine N-oxide (TMAO), and astaxanthin is passed to a desalting zone 201. In the desalting zone, a simulated moving bed zone provides the separation of the salts and TMAO from the krill oil extract to provide a waste stream in line 112 consisting essentially of the salts and TMAO, and a desalted krill oil stream in line 118, comprising neutral lipids, polar lipids, and astaxanthin. The waste stream 112 is passed to proper safe disposal in any conventional manner. The desalted krill oil stream in line 118 which typically comprises about 30 to about 40 weight percent polar lipids on a dry basis is either optionally withdrawn as a desalted krill oil rich stream via lines 118, 114 and 120, or passed via line 116 to a fixed bed Polar Lipid extraction zone 202. In the fixed bed Polar Lipid extraction zone, the desalted krill oil stream is subjected to selective adsorption and desorption steps over the fixed bed Polar Lipid extraction zone 202 with solvents to provide a polar lipid extract stream in line 124 comprising polar lipids on a dry or solvent free basis. The fixed bed Polar Lipid extraction zone 202 contains a selective adsorbent comprising a macroporous styrenic polymeric bead type resin such as DIAION HP 20 (Available from Mitsubishi Chemical Corporation, Virginia) for hydrophobic compounds. Preferably, the polar lipid extract stream comprises at least 50 wt-% polar lipids on a solvent free basis. More preferably, the polar lipid extract stream comprises at least 60 wt-% polar lipids on a solvent free basis. Most preferably, the polar lipid extract stream comprises at least 90 wt-% polar lipids on a solvent free basis. All or a portion of the polar lipid extract stream in line 124 may be admixed via lines 126 and 126 in any proportion with at least a portion of the desalted 40 percent krill oil rich stream via lines 114 and 122 to provide one or more intermediate quality krill oil rich stream in line 128 having a polar lipid content between 40 wt-% and 99 wt-% polar lipids on a dry or solvent free basis. More preferably, the intermediate quality krill oil rich stream in line 128 has a selected concentration of polar lipids which on a solvent free basis comprise 99, 95, 90, 85, 80, 75, 70, 65, 60, 55 and 50 wt-% polar lipids on a dry or solvent free basis. The fixed bed Polar Lipid extraction zone 202 further provides a neutral lipid raffinate stream in line 132 comprising neutral lipids and astaxanthin, and is essentially free of polar lipids. In the neutral lipid raffinate, the term "essentially free of polar lipids" means that the neutral lipid raffinate stream comprises less than about 0.5 wt-% polar lipids on a solvent free basis. More preferably, the term "essentially free of polar lipids" means that the neutral lipid raffinate stream comprises less than about 0.1 wt-% polar lipids on a solvent free basis. The neutral lipid raffinate stream in line 132 is passed to an astaxanthin separation zone 203 wherein the neutral lipid raffinate stream comprising neutral lipids and astaxanthin is subjected to a solid bed extraction process wherein the neutral lipid raffinate stream is contacted with a selective adsorbent for the adsorption of astaxanthin. Applicant discovered that astaxanthin could be selectively adsorbed from the neutral lipid raffinate stream over a selective adsorbent comprising or consisting of activated carbon having a particle size of 40×70 microns to provide a second neutral lipid raffinate stream 134 comprising or consisting essentially of neutral lipids on a solvent free basis. It was discovered that the adsorbed astaxanthin could be desorbed from the selective activated carbon adsorbent using as selective desorbent, anisole, and desorbing the adsorbed astaxanthin with anisole, a Gras solvent, to provide an astaxanthin stream in line 136. The term Gras is a US Food and Drug Administration (FDA) designation which means that the solvent is generally recognized as safe. The astaxanthin separation zone 103 operates as a swing bed adsorption process comprising a plurality of astaxanthin adsorption beds wherein the neutral lipid raffinate stream is passed to at least one astaxanthin adsorption bed to provide a neutral lipid stream comprising neutral lipids and solvent in line 134. On regeneration of the at least one astaxanthin adsorption bed with the anisole solvent, an astaxanthin stream is withdrawn in line 136. The astaxanthin separation can be operated as a continuous or semi-continuous process by providing a sufficient number of astaxanthin adsorption beds to process the neutral lipid raffinate stream while a one or more astaxanthin adsorption beds is isolated and regenerated. During regeneration the isolated astaxanthin adsorption bed is flushed with anisole solvent to recover the adsorbed astaxanthin. Following solvent removal, the neutral lipid stream in line 134 following optional solvent removal may be employed for biodiesel production. The astaxanthin recovered from this process is of high purity (100, 99.5, 99, 98, 97, 96, 95 wt-% on a solvent free basis) and following optional solvent removal can be employed in the food and pharmaceutical industries. Recovery of the astaxanthin is greater than or equal to 99 wt-% based on the astaxanthin in the neutral lipid raffinate stream in line 132.

Figure 2:
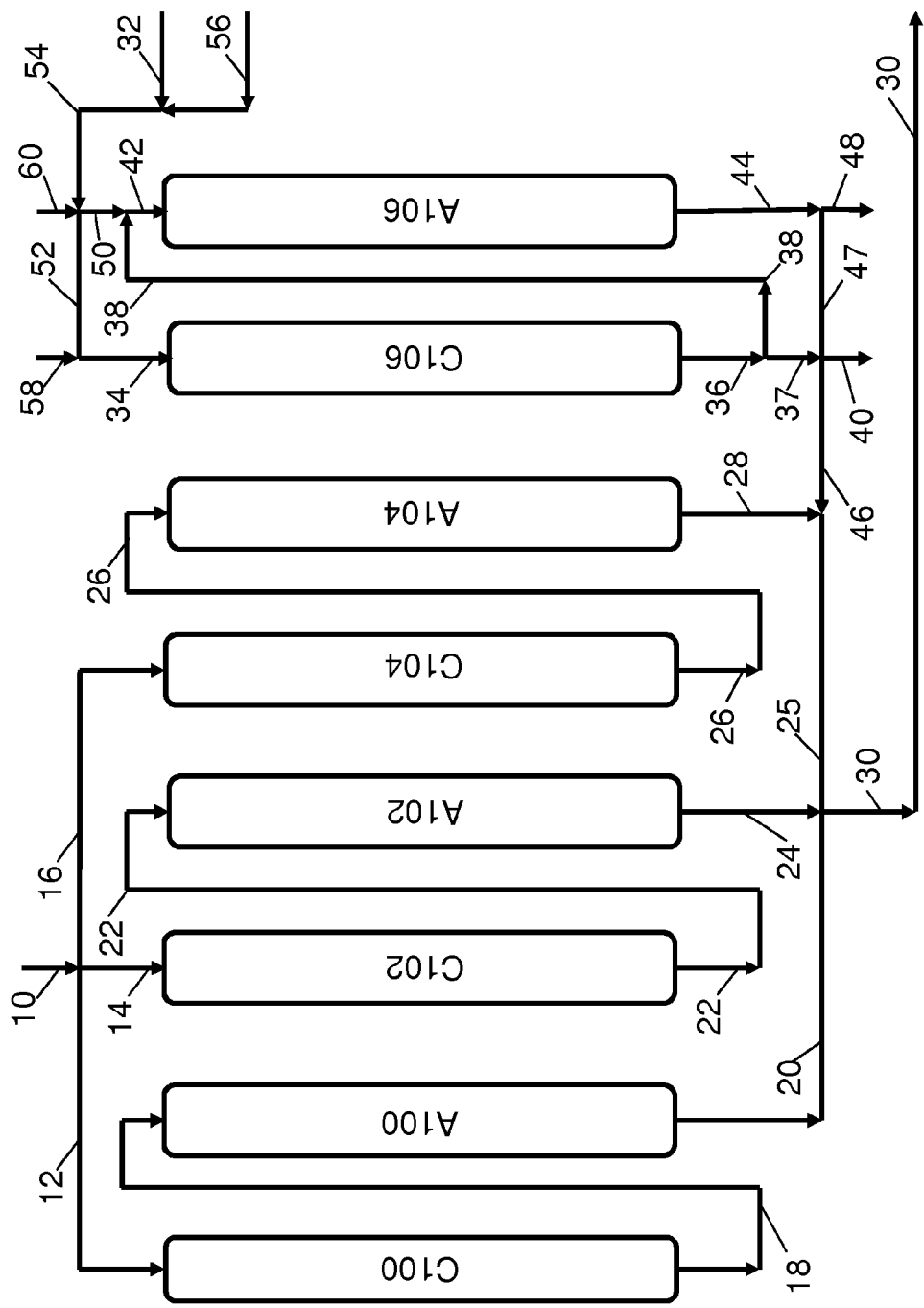
FIG. 2 is a schematic block flow diagram illustration of one embodiment of the invention showing the process of the desalting zone using a simulated moving bed system.

FIG. 2, illustrates one embodiment of the krill oil simulated moving bed desalting process of the present invention. For clarity, the complex system of pumps and valves has not been shown in FIG. 2. The process is carried out as an isothermal process at atmospheric pressure or above, and at a desalting temperature ranging from about 15 to about 45° C. More preferably, the desalting temperature ranges between about 20 and about 40° C. The process streams to be desalted and the desalted lipid rich stream are maintained in the liquid state. Prior to desalting, a krill extract stream is diluted with a solvent stream to provide a diluted krill oil stream having a krill oil concentration of between about 4 percent by weight and up to about 7 percent by weight. More preferably, diluted krill oil stream has a concentration of about 5 percent by weight in the solvent stream. The solvent stream for food grade products has an ethanol to water ratio of from about 99:1 to about 95:5. More preferably, the solvent stream will have a ratio of ethanol to water of 96:4, 97:7, or 98:2. Most preferably, the solvent stream will have a ratio of ethanol to water of 98:2. To minimize operating difficulties is passing the diluted krill oil through a packed bed of adsorbent, the diluted krill oil is filtered through a 1 to 0.45 micron filter or passed through an optional guard bed to provide the krill oil desalter feed stream. With reference to FIG. 2, a crude krill oil, or krill oil extract feed stream to be desalted comprising solvent, neutral lipids, polar lipids, salts, trimethylamine N-oxide (TMAO), and astaxanthin is passed via line 10 to a desalter zone (shown as 201 in FIG. 1) having a parallel arrangement of a plurality of desalting stages. Each desalting stage contains cation column containing a cation adsorbent and an anion column containing an anion adsorbent. Each cation and each anion column has a top, and a bottom. In the simulated moving bed process of the present invention one or more of desalting stages will be actively desalting, while at least one desalting stage will be undergoing regeneration. Preferably, at least 3 desalting stages are actively desalting the krill oil desalter feed stream, and at least one desalting stage is being regenerated. At the completion of the regeneration cycle, the last desalting stage in the series of parallel desalting stages will be rotated to regeneration and the newly regenerated desalting stage will be rotated to the position of the first desalting stage. As shown in FIG. 1, three desalting stages: Stage 1 (C100/A100), Stage 2 (C102/A102), and Stage 3 (C104/A104) are 3 active desalting stages, and one stage, Stage 4 (C106/A106) is undergoing regeneration. During active desalting, the crude krill oil feed stream in line 10 is passed to the top of a first stage cation column C100, and the first stage cation effluent is withdrawn from the bottom of the first cation column and passed to the top of the first stage anion column A100 via line 18. The first stage anion effluent is withdrawn in line 20 from the bottom of the first stage anion column A100 and passed to line 30 and withdrawn as a desalted lipid rich stream. Similarly, and in parallel, the crude krill oil stream is passed to additional desalting stages, shown in FIG. 1 as Stage 2 (C102/A102), and Stage 3 (C104/A104). Thus, in Stage 2, the krill oil stream is passed via lines 10 and 14 to the top of the second stage cation column C102 and the second stage cation effluent is withdrawn from the bottom of the second stage cation column C102 and passed to the top of the second stage anion column A102 via line 22. The second stage anion column effluent is withdrawn in line 24 and combined with the first stage anion effluent in line 30 as desalted lipid rich stream. In Stage 2, the krill oil stream is passed via lines 10 and 16 to the top of the third stage cation column C104 and the third stage cation effluent is withdrawn from the bottom of the third stage cation column C104 and passed to the top of the third stage anion column A104 via line 26. The third stage anion column effluent is withdrawn in lines 28 and 25, before being admixed with the first and second stage anion effluents in line 30 and withdrawn as desalted lipid rich stream. The desalted lipid rich stream comprises neutral lipids, polar lipids, and astaxanthin, and is substantially free of salt and TMAO. The term substantially free of salt and TMAO means that the desalted lipid rich stream comprises less than about 10 ppm by weight. More preferably, the term substantially free of salt and TMAO means that the desalted lipid rich stream comprises less than about 5 ppm by weight on a dry basis. Most preferably, the term substantially free of salt and TMAO means that the desalted lipid rich stream comprises less than about 1 ppm by weight on a dry basis. The desalted liquid rich stream may be passed to an evaporator to recover at least a portion of the mobile phase solvent and provide a concentrated desalted krill oil product stream. Preferably the concentrated desalted krill oil product stream has a conductivity (μS/cm) of less than about 3.32. The regeneration of stage 4 takes place in 5 steps, while the desalting Stages 1 to 3 continue operating in active desalting mode. The desalting regeneration cycle includes the following steps:

A) Solvent flushing,
B) Water wash,
C) Ion Reactivation,
D) Second Water wash, and
E) Reconditioning.

In step (A), the exhausted desalting stage 4 is first flushed with a solvent stream to recover any desalted lipids remaining in the adsorbent columns (C106/A106) in Stage 4. In the Solvent flushing step, a mobile phase solvent comprising an alcohol and water having a ratio of 95 parts alcohol to 5 parts water to 99 parts alcohol to 1 part water (such as 95:5, 96:4, 97:3, 98:2, and 99:1) is passed in lines 32, 54, and 34 to the top of the fourth stage cation column C106 and the fourth stage effluent is withdrawn from the bottom of the fourth stage cation column C106 and passed to the top of the fourth stage anion column A106. The effluent from the fourth stage anion column A106 is passed via lines 44, 47, 46, and 25 to be admixed with the effluents from Stages 1-3 and is withdrawn as desalted lipid rich stream. At the end of the Solvent flushing step (A), the flow of mobile phase solvent in line 32 is terminated and Stage 4 is water washed in a Water Wash step (B). In the Water Wash step (C) both the fourth stage cation column and the fourth stage anion column A106 are water washed by introducing a water wash stream via lines 56, 54, 50 and 42 to the top of the fourth stage anion column A106, and via lines 56, 54, 52, and line 34 to the top of the fourth stage cation column C106. The effluent from the fourth stage cation column C106 is withdrawn via lines 36, 37, and 40, and the effluent from the fourth stage anion column is withdrawn via lines 44 and 48 and passed to waste disposal as a first waste stream. The water wash is terminated and the water washed fourth stage cation and anion columns are ion reactivated separately in an Ion Reactivation step (C). In the Ion Reactivation step (C), an acid stream in line 58 comprising about 2 to about 6 weight percent hydrochloric acid (HCl) solution in water is passed via lines 54 and 34 to the top of cation column C106 and a spent acid regenerant stream is withdrawn via lines 36, 37, and 40 and passed to waste disposal as a second waste stream. In parallel, and simultaneously with the ion regeneration of the cation column C106, a basic ion stream comprising from about 5 to about 8 weight percent solution of sodium carbonate ($Na_2CO_3$) in water is passed to the top of the anion column A106 via lines 60, 50, and 42, and a spent basic ion stream is withdrawn from the anion column A106 and passed to waste disposal via lines 44 and 48 as a third waste stream. The Ion Reactivation step (C) is continued until the adsorbent columns C106 and A106 are returned to effective ion exchange strength. At the completion of the Ion Reactivation step, the passing of the acid regenerant stream and the basic ion stream are terminated. A second Water wash step (D) operates in the same manner as described hereinabove in step (B). In the second Water wash step (D), both the fourth stage cation column and the fourth stage anion column A106 are separately water washed to remove excess ions by introducing a water wash stream via lines 56, 54 and 42 to the top of the fourth stage anion column A106, and via lines 56, 54, 52, and line 34 to the top of the fourth stage cation column C106. The effluent from the fourth stage cation column C106 is withdrawn via lines 36, 37, and 40, and the effluent from the fourth stage anion column is withdrawn via lines 44 and 48 and passed to waste disposal as a fourth waste stream. The second Water wash step (D) is terminated and the water washed fourth stage cation and anion columns are conditioned in a Reconditioning step (E). In the Reconditioning step (E), mobile phase solvent comprising an alcohol and water having a ratio of 95 parts alcohol to 5 parts water to 99 parts alcohol to 1 part water (such as 95:5, 96:4, 97:3, 98:2, and 99:1) is passed in lines 32, 54, 52, and 34 to the top of the fourth stage cation column C106 and via lines 32, 54, and 40 to the top of the fourth stage anion column A106. More preferably, the mobile phase solvent comprises 98 parts alcohol to 2 parts water. The effluent from Stage 4 cation column C106 is passed via lines 36, 37, 47, and 48 to waste disposal, and the effluent from the Stage 4 anion column is passed via line 44, where it is admixed with the effluent from the Stage 4 cation column C106 as a fifth waste stream and passed to waste disposal via line 48. All of the waste streams comprise water, salt and TMAO. The waste streams 1-5 are combined into a single waste effluent stream, and optionally, at least a portion of the water in the single waste effluent stream is recovered by distillation or evaporation at a pressure below atmospheric pressure and the recovered water returned to the process as recycled water. At the end of the regeneration cycle, Stage 4 is fully regenerated and the desalting stages are cycled by shifting the newly regenerated Stage 4 to the lead position and desalting Stages 1-3 are shifted to the right such that Stage 3 will be regenerated, and the remaining stages. Now Stage 4, Stage 1, and Stage 2 are in parallel. The process continues in a continuous manner and at the end of each regeneration cycle, the desalting stages are shifted to the right and the newly regenerated desalting stage is placed in the lead or first position and the last active desalting stage is shifted to the regeneration mode.

Figure 3:
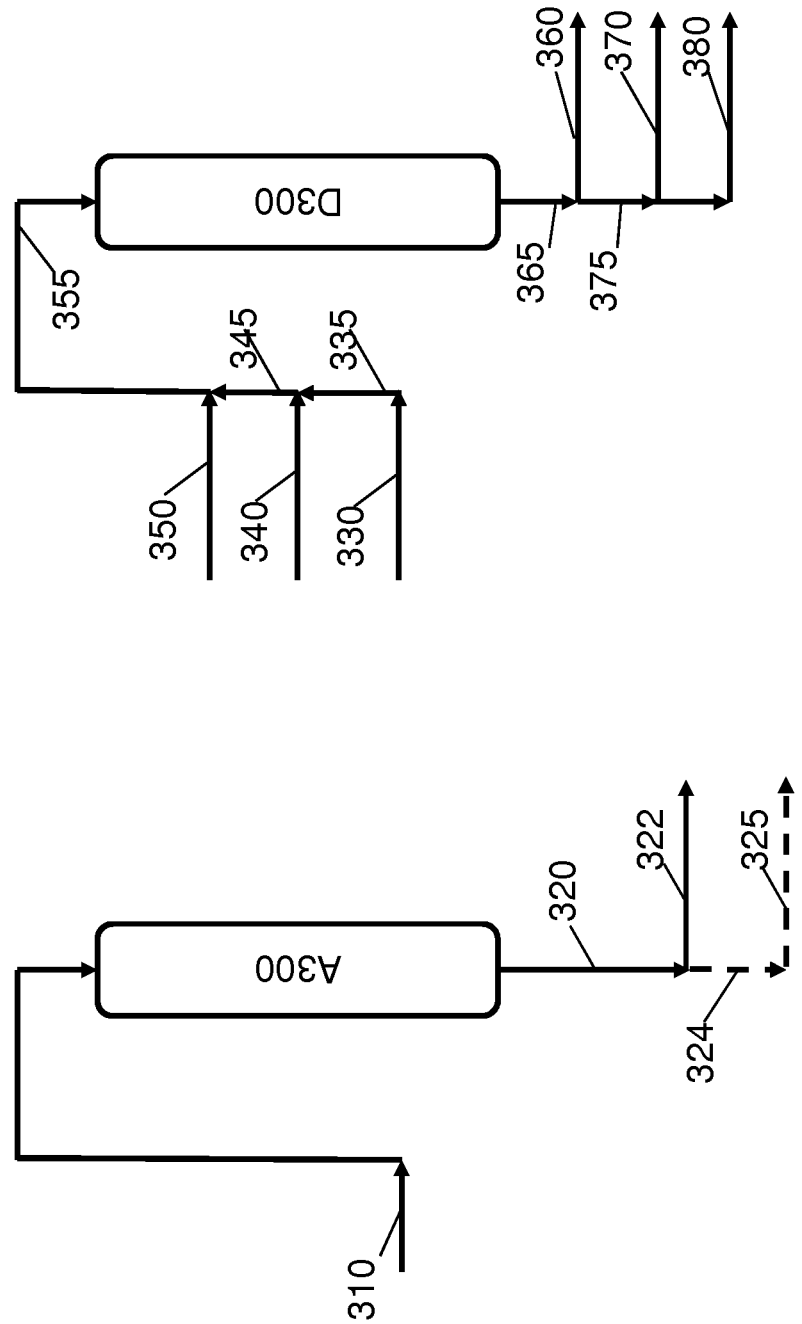
FIG. 3 is a schematic block flow diagram illustration of one embodiment of the invention showing a fixed bed Polar Lipid extraction zone with regeneration.

FIG. 3 is a schematic block flow diagram illustrating one embodiment of the fixed bed Polar Lipid extraction zone (described hereinabove in FIG. 1 as 202) for the separation of polar lipids from neutral lipids over a fixed bed adsorbent consisting of a macroporous styrenic polymeric bead type resin such as DIAION HP 20 (Available from Mitsubishi Chemical Corporation, Virginia). According to FIG. 3, the desalted krill oil stream 310 is subjected to selective adsorption over the macroporous styrenic polymeric bead type resin by passing the desalted krill oil stream through the fixed bed adsorption zone A300 wherein the neutral lipid and astaxanthin are retained and to provide a fixed bed extract stream comprising polar lipids in line 320. The desalted krill oil stream in line 310 diluted to a concentration of about 5 percent by weight on a dry basis in the solvent stream. The desalted krill oil stream in line 310 may also be directly withdrawn from the desalting zone without solvent recovery and passed to the fixed bed Polar Lipid extraction zone. The solvent stream for food grade products has an ethanol to water ratio of from about 99:1 to about 95:5. More preferably, the solvent stream will have a ratio of ethanol to water of 96:4, 97:7, or 98:2. Most preferably, the solvent stream will have a ratio of ethanol to water of 98:2. The polar lipid or fixed bed extract stream comprising polar lipids is withdrawn from adsorption zone A300 in line 320. It was discovered that one polar lipid species, LPC, appears in the first bed volume withdrawn in the fixed bed extract stream 320. All or a portion of the first bed volume may be excluded from the polar liquid rich stream 322 by optionally passing at least a portion of the first bed volume via lines 324 and 325 to either withdraw an LPC rich stream as a separate LPC product stream after solvent removal or disposed of as a component of biodiesel. Following a period of adsorption, the adsorption bed A300 is isolated and is subject to regeneration. In regeneration, the neutral lipids, now loaded on the adsorbent in the isolated bed D300 are first desorbed with the introduction of solvent in line 350 and 355 to desorb the adsorbent neutral lipids and to provide a neutral lipid raffinate stream via lines 365 and 360 comprising neutral lipids and astaxanthin. Isolated bed D300 is then subjected a hot regeneration with the passing of a hot ethanol stream having a regeneration temperature of between about 40° C. and about 60° C. via lines 340, 345, and 355 to desorb any remaining neutral lipids and astaxanthin via lines 365, 375 and 370 to provide a spent first NL regen stream in line 370. The isolated bed D300 is then subjected to a cool down step by introducing an cold ethanol stream at a cooling temperature between about 15 and 25° C. via lines 330, 335, 345 and 355 to isolated bed D300 and withdrawing a second NL regen stream via lines 365, 375 and 380. The first NL regen stream may be combined with the neutral lipid raffinate stream and the second NL regen stream may be recycled to be combined with the desalted krill oil stream.

Figure 4:
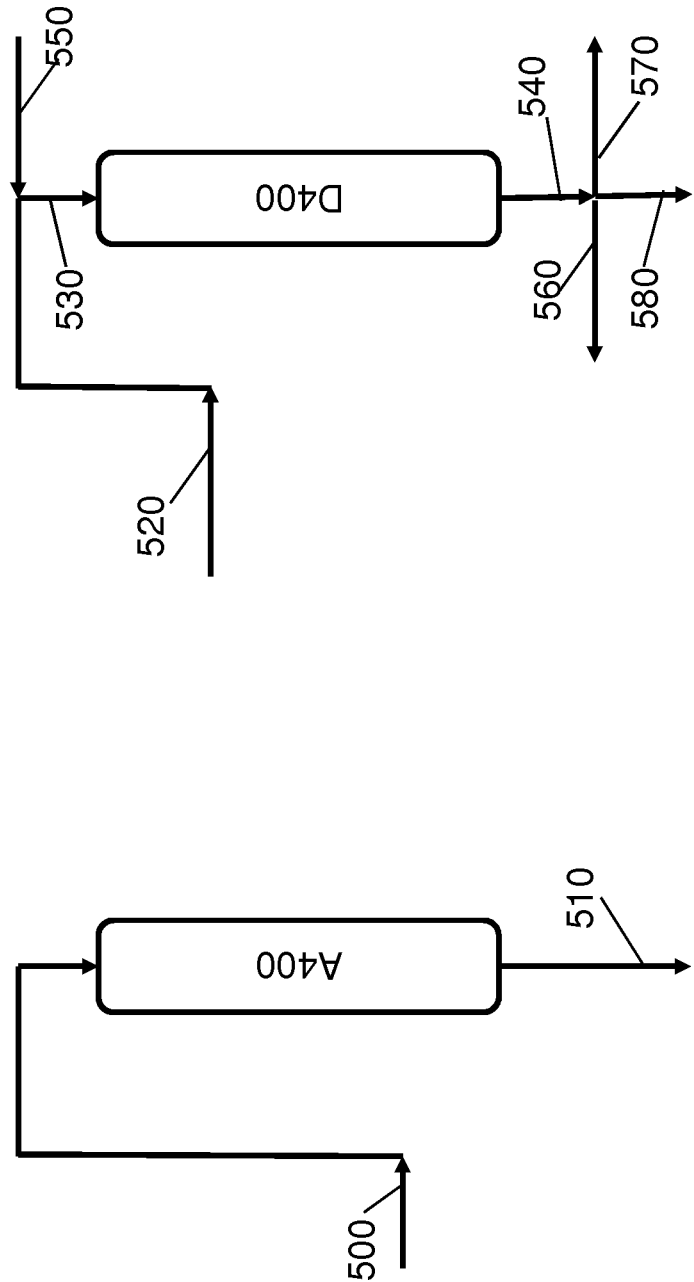
FIG. 4 is a schematic block flow diagram illustration of one embodiment of the invention showing an astaxanthin separation zone with regeneration.

FIG. 4 is a schematic block flow diagram illustrating one embodiment of the Astaxanthin Separation zone (described hereinabove in FIG. 1 as 203) for the separation of astaxanthin from neutral lipids over a fixed bed adsorbent comprising or consisting of a steam activated carbon adsorbent. According to FIG. 4, the neutral lipid raffinate stream comprising solvent, neutral lipids and astaxanthin in line 500 is passed to astaxanthin adsorber A400 and therein, astaxanthin is adsorbed on the steam activated carbon and neutral lipids are rejected and are withdrawn as a neutral lipid rich stream in line 510 comprising solvent and neutral lipids. The neutral lipid raffinate stream is diluted to a 5 wt-% on a dry basis in an ethanol/water solvent. Following removal of solvent from the neutral lipid rich stream by evaporation at low temperature, a neutral lipid product stream is provided which can be passed to a biodiesel production facility. Before the breakthrough of astaxanthin, which can be detected by a change in the color of the neutral lipid rich stream, the adsorber bed is shifted to a regeneration mode, shown as regen adsorber D400. The regeneration of the now astaxanthin loaded adsorber D400 comprises, flushing the regen adsorber D400 with anisole via lines 520 and 530 to desorb the astaxanthin and withdraw a first astaxanthin effluent stream comprising anisole and astaxanthin via lines 540 and 580. The regen adsorber D400 is purged by introducing nitrogen to the top of the regen adsorber D400 via lines 550 and 530 to remove any remaining anisole via lines 540 and 560 to provide an anisole return stream which is recovered for reuse as a portion of the anisole solvent. The regen adsorber is dried by continuing the introduction of nitrogen via lines 550 and 530, and the gaseous effluent is passed to safe disposal. Optionally, ethanol can be employed as an additional purge stream, if required. Following removal of the anisole solvent, an astaxanthin product was recovered.

The present invention is further described and illustrated by the following examples.

EXAMPLES

Example 1

Desalting of Krill Oil Extract

Approximately 70 g of DOWEX MONOSPHERE 88 (Available from The Dow Chemical Company) a strong acid cation resin and DOWEX MONOSPHERE 77 (Available from The Dow Chemical Company) a weak base anion resin were slurry packed in separate 114 mL capacity 300×22 mm stainless steel columns having an ID of 22 mm and a length of 300 mm. The columns were separately washed with about 2 bed volumes of 100% ethanol to remove any impurities from the resins. The amount of the leaching contaminants was tracked by measuring the absorbance by a UV-Vis spectrophotometer SPECTRA MAX Plus (Available from Molecular Devices, Sunnyvale, Calif.) at a wavelength of 260 nm. When the absorbance reached within 20% of absorbance of pure ethanol the washing of each resin column was stopped.

Desalting Regeneration

The resin columns were regenerated separately prior to use by flushing the cation column with 2 bed volumes (BV) of 7% by wt. HCl) column and flushing the anion column with 2 BV of 4% by wt. sodium carbonate solution. This regeneration step was required to ensure that the cation column was at full capacity and to exchange the OH⁻ groups on the anion exchange column with a carbonate $CO_3^{2-}$ ion. Flow rate was 1 ml/min. All water used in was HPLC grade. The cation column and the anion column were separately washed with 2 BV of HPLC water and then conditioned with about 2 BV of a 98/2 w/w ethanol/water solution to flush any remaining water from the cation and anion columns.

Feed Processing

Figure 5:
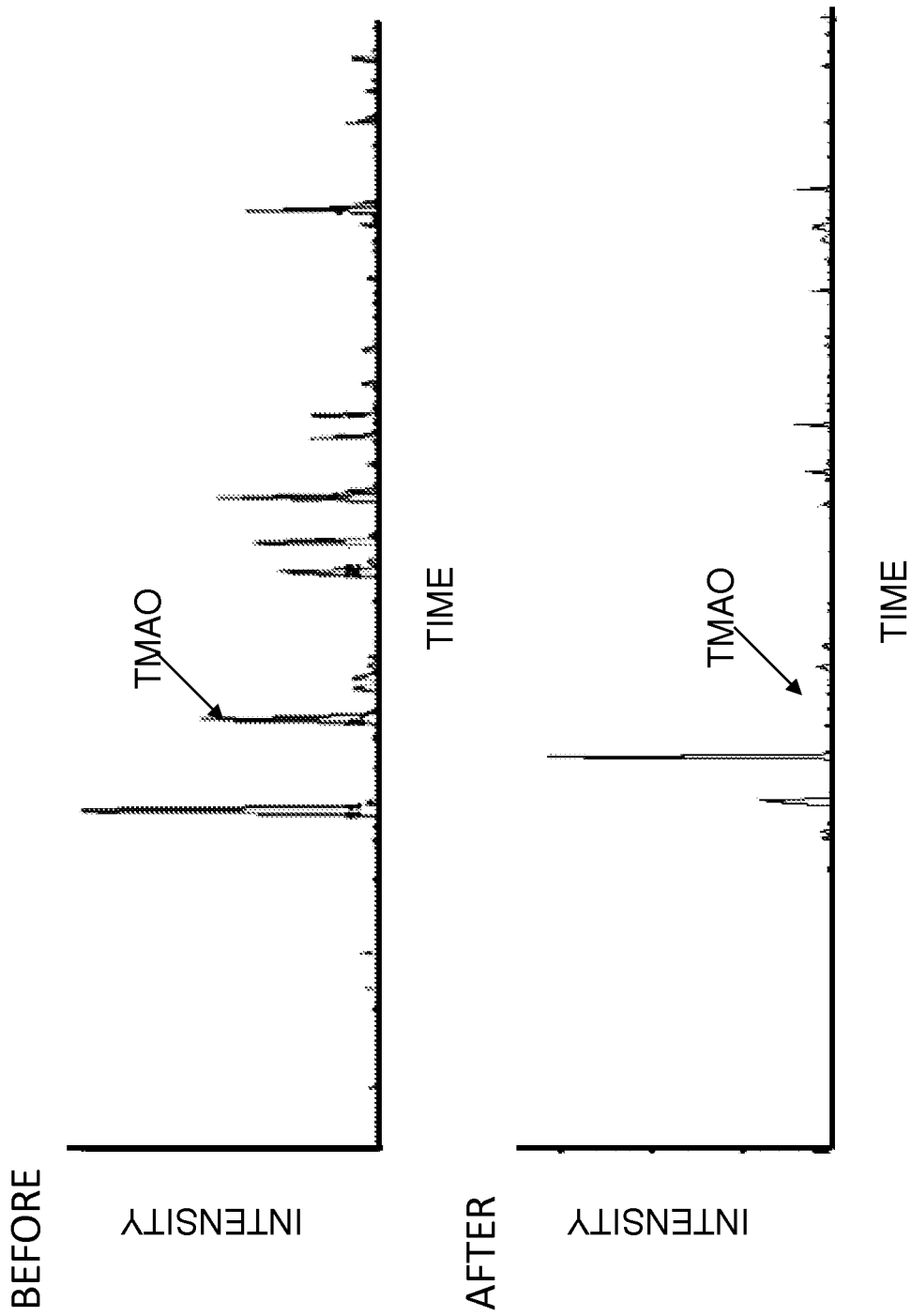
FIG. 5 is an HPLC chromatogram showing the TMAO content of krill oil extract before and after desalting.
Figure 6:
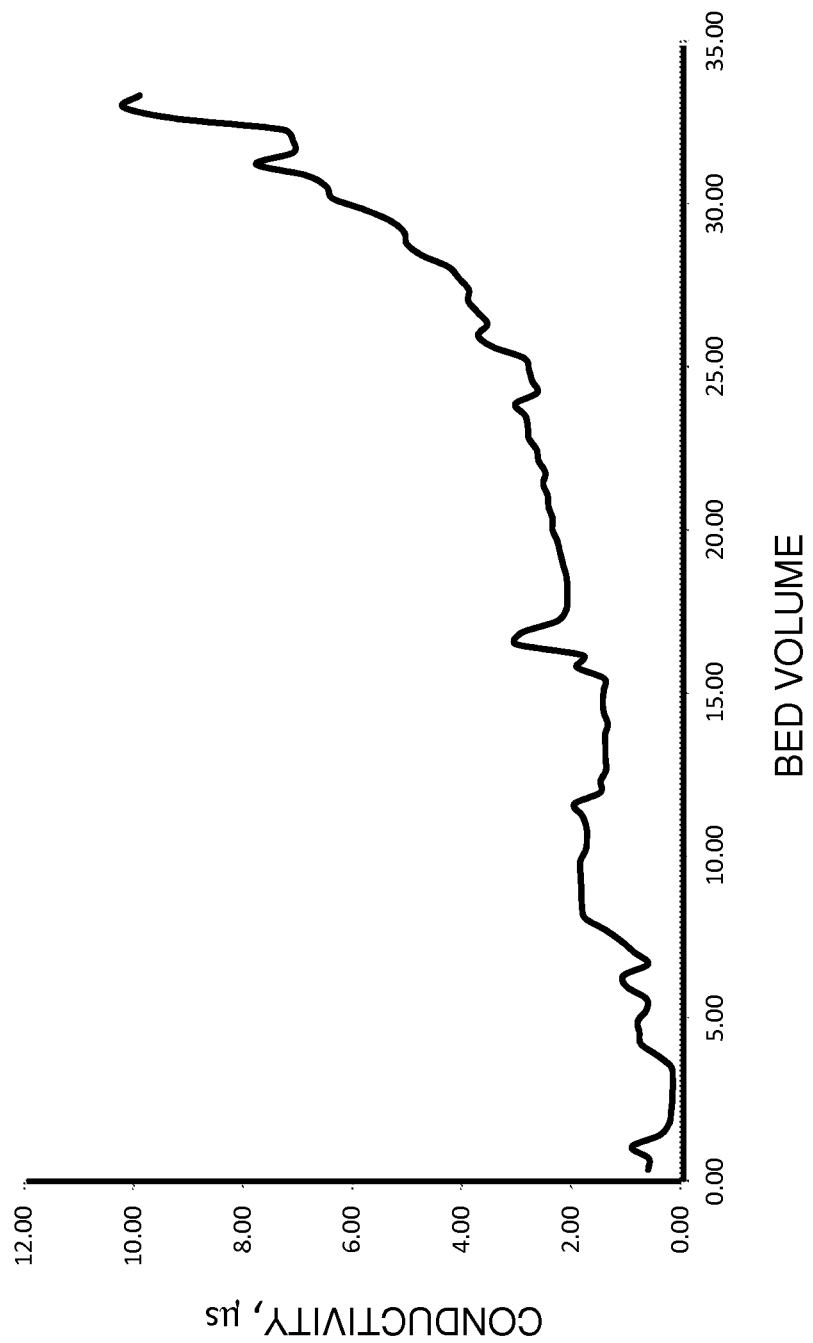
FIG. 6 is a chart showing the conductivity of the effluent from the desalter as a function of bed volume of feed processed.

The cation and anion columns were then connected in series with the outlet of the cation column connected to the inlet of the anion column and the outlet of the anion column connected to a fraction collector. A 5 wt-% dry mass feed stream was prepared by dissolving a sufficient quantity of dry Krill Meal Extract in a solution of 98/2 w/w Ethanol/water to arrive a 5 wt-% dry mass of krill oil extract in the krill oil feed stream. The krill oil feed stream was then loaded onto the serial arrangement of the cation/anion columns at a flow rate of about 5 ml/min. Eluate fractions were collected every 0.35 BV (40 mL). Conductivity was measured in each collected fraction. TMAO detection tests were also conducted to verify TMAO removal by means of a triple quadrupole mass spectrometer API 3000 (Available from Applied Biosystems, Carlsbad, Calif., US). TMAO can be detected in a Q1MS positive ion mode as m/z 76 upon direct injection of 20 μL of sample using the autosampler followed by elution with ethanol (containing 0.1% of formic acid) at 0.3 mL/min into the turbospray ion source. When the conductivity of the eluates reached a value of 20 μs, the feed loading was stopped. The columns were then flushed with a solution of 98/2 w/w Ethanol/water 10 BV to remove any lipids remaining adsorbed in the columns and treated as a separate fraction. The cation and anion columns were isolated and the regeneration procedure described hereinabove was repeated to restore the activity of the cation and anion resin columns. FIG. 5 illustrates the essentially complete removal TMAO from krill oil extract where the TMAO peak is present in the krill oil feed, but no TMAO peak is present in the desalted product. Using the above steps, the cation and anion column loaded with cation resin and anion resin as described hereinabove effectively desalted approximately 35 bed volumes of the 5 wt % Krill Meal Extract in a solution of 98/2 w/w Ethanol/water, completely removing essentially all salts and TMAO; that is, there was no detectable breakthrough of salt or TMAO in the eluate. FIG. 6 is a chart of the conductivity of the fractions collected as a function of the krill oil extract feed processed through the desalter showing the breakthrough of salts after the passage of about 35 bed volumes of feed. Alternate cation exchange resins including DOWEX 650 C (Available from The Dow Chemical Company) and PK 228 (Mitsubishi Chemicals, Japan) were tested with similar results for removal of salt and TMAO, but showed a slightly lower capacity. Alternate Anion Exchange resins including AMBERLIGHT IRA-900 (Available from GFS Chemicals, Inc. Powell, Ohio), a strongly basic resin of moderately high porosity with benzyltrialkyl-ammonium functionality were tested with similar results with only with a slightly lower capacity.

Example 2

Desalter Operation Material Balance

The desalting operation of the present invention is further illustrated for a simulated moving bed desalting plant processing 1500 MTA (Metric Tonnes per Annum) of crude krill oil meal extract as described hereinabove in FIG. 2. The material balance shown in Example 2 is based on the results of the desalting operation described and demonstrated in Example 1. The crude krill oil meal extract has the following composition:

| Component: | Kg/hour | Wt-% |
|---|---|---|
| Polar Lipids (PL) | 59.58 | 28.65 |
| Neutral Lipids (NL) | 138.75 | 66.68 |
| Astaxanthin | 0.21 | 0.06 |
| Salt | 7.29 | 3.47 |
| TMAO | 2.5 | 1.2 |
| Total | 208.12 | 100.0 |

The crude krill oil meal extract is diluted to about 5 weight percent in a mobile phase solvent by admixing the crude krill oil meal extract with 4068 Kg/hour of a mobile solvent stream comprising 98 parts ethanol to 2 parts water, and filtering the diluted krill oil stream through a 1 micron filter to provide a filtered krill oil feed stream. The filtered krill oil feed stream is passed to a simulated moving bed desalting unit having 4 desalting stages as described in FIG. 2. Each of the desalting stages comprises a cation zone and an anion zone, and during the active desalting process for 3 of the four stages, the filtered krill oil feed stream is introduced at the top of the cation zone and the effluent from the bottom of the cation zone is introduced directly to the top of the anion zone, and the effluent from the bottom of the anion zone is collected and passed to a desalted lipid collection zone. Three of the desalting stages operated in parallel. The fourth stage was regenerated during the period when the other three stages processed the filtered krill oil feed stream. The desalted krill oil had the following composition on a dry basis after the desalting process:

| Component: | Kg/hour | Wt-% |
|---|---|---|
| Polar Lipids (PL) | 59.58 | 30.01 |
| Neutral Lipids (NL) | 138.75 | 69.89 |
| Astaxanthin | 0.21 | 0.11 |
| Salt | 0 | 0 |
| TMAO | 0 | 0 |
| Total | 198.54 | 100.0 |

A reject stream comprising the TMAO and salt in the amount of about 992 kg/hr is withdrawn from the desalting process. The reject stream on a dry basis has the following composition:

| Component: | Kg/hour | Wt-% |
|---|---|---|
| Salt | 7.29 | 0.73 |
| TMAO | 2.5 | 0.25 |

-continued

| Component: | Kg/hour | Wt-% |
|---|---|---|
| Water | 967.04 | 97.48 |
| HCL | 8.27 | 0.83 |
| NaOH | 6.89 | 0.69 |
| Total | 198.54 | 100.0 |

Example 3

Purification of PL by HP-20 Resin in Fixed Bed Extraction

Purification of polar lipids (PL) was carried out using the desalted krill oil of Example 1. Approximately 70 grams of DIAION HP-20 a styrene-divinylbenzene (Available from Mitsubishi Chemical, Japan) was slurry packed in a 300×22 mm stainless steel column using 100% pure ethanol. The column was washed with 2 bed volumes (BV) of ethanol to remove any impurities from the resin. The amount of the leaching contaminants was tracked by measuring the absorbance by a UV-Vis spectrophotometer SPECTRA MAX Plus (Available from Molecular Devices, Sunnyvale, Calif.) at wavelength of 260 nm. When the absorbance reached within 20% of absorbance of pure ethanol the washing was stopped. The desalted krill meal Extract was diluted with a sufficient amount of 98/2 w/w ethanol/water to provide 5% dry mass dissolved in the 98:2 ethanol:water solvent to provide the feed to the polar lipid purification process. Feed was charged to the column at a flow rate of 5 ml/min and 0.35 BV (40 mL) fractions were collected. The lipid profile was tracked qualitatively by HPLC-UV-Vis at a wavelength of 215 nm on a 5 μm C18 silica HPLC column 150 mm×4.6 mm (Available from Orochem Technologies, Inc, Naperville, Ill.). A gradient starting at 80/20 vol./vol. ethanol/water and eventually changing to 100% ethanol was used to separate the polar lipids from the non-polar lipids. All chromatography tests were conducted on an AGILENT 1100 series HPLC (Available from GMI, Inc., Ramsey, Minn.). When the Non-polar lipids began to elute as detected by the HPLC test, the feed loading was stopped. A solution of 80/20 w/w ethanol/water was used to flush most of the remaining polar lipids from the column. A solution of 98/2 w/w Ethanol/water was used to flush any remaining polar lipids from the column and remove some of the non-polar lipids. Acetone was then used to remove any remaining mass from the column including non-polar lipids and astaxanthin. Using the HPLC chromatograms and the concentration of each fraction in mg/mL was determined. A determination of which fractions were to be mixed to make a final composition of PL 60% NL 40% in the product was made and the appropriate fractions were combined. The fractions from bed volumes 2-5 were combined to provide the final product having a PL content of 60.1 wt-% on a dry basis. FIG. 7 is an HPLC chromatogram of the desalted krill oil feed to the fixed bed extraction zone of Example 3 for extraction of polar lipids. FIG. 8 is an HPLC chromatogram of the extract product of Example 3 from the fixed bed extraction zone having a reduced amount of neutral lipids relative to the amount of neutral lipids in the feed. Lyso-phospholipids (such as LPC) are the oxidized products of phospholipids presented in crude krill meal extract, and should be reduced. HP 20 resin can separate LPC from rest of the polar lipids (PL). Because the eluate fraction derived from the $1^{st}$ bed volume contained significant amount of LPC, eliminating or removing the first bed volume as a separate LPC product, significantly reduces the LPC content in the final polar lipid product.

Example 3a

Example 3a

Purification of PL

Purification of polar lipids (PL) in krill oil extract was carried out over a fixed bed of using the desalted krill oil of Example 1. A stainless steel column having an inside diameter of about 15 cm (6 inches) and a length of about 91 cm (36 inches) was loaded with about 16 liters of DIAION HP-20 a styrene-divinylbenzene resin (Available from Mitsubishi Chemical, Japan.) The column was conditioned with 98/2 ethanol/water mixture to remove any impurities from the resin. Five bed volumes (about 80 Liters) of desalted krill meal dissolved in a 98/2 ethanol/water mixture to a concentration of 36.5 grams/L and having a polar lipid (PL) content of 40 wt-% (w/w) on a dry basis was passed to the column at room temperature. The column was then washed with an 80/20 ethanol/water mixture for 3 bed volumes and the effluent collected in eight fractions. Each fraction was analyzed for the amount of dry mass in each fraction and the PL content was determined by NMR analysis technique. The PL content of each fraction collected during the loading steps and the 80/20 wash steps is shown on the following table. The recovered polar lipid analysis shows that the fixed bed extraction of polar lipids over the styrene-divinylbenzene resin should significant recovery of polar lipids at a purity level of about 90 wt-% on a dry basis.

| Column Loading | Bed Volume | Solid Content Gram/L | Polar Lipid, wt-% |
|---|---|---|---|
| LOADING STEPS | 1 | 1.9 | |
| | 2 | 15.1 | 79.58 |
| | 3 | 24.9 | 69.37 |
| | 4 | 26.5 | 57.66 |
| | 5 | 30 | 49.7 |
| 80/20 Ethanol/Water wash | 6 | 25.2 | 4787 |
| | 7 | 1.2 | |
| | 8 | 1.5 | |

Example 4

Extraction of Astaxanthin

Figure 9:
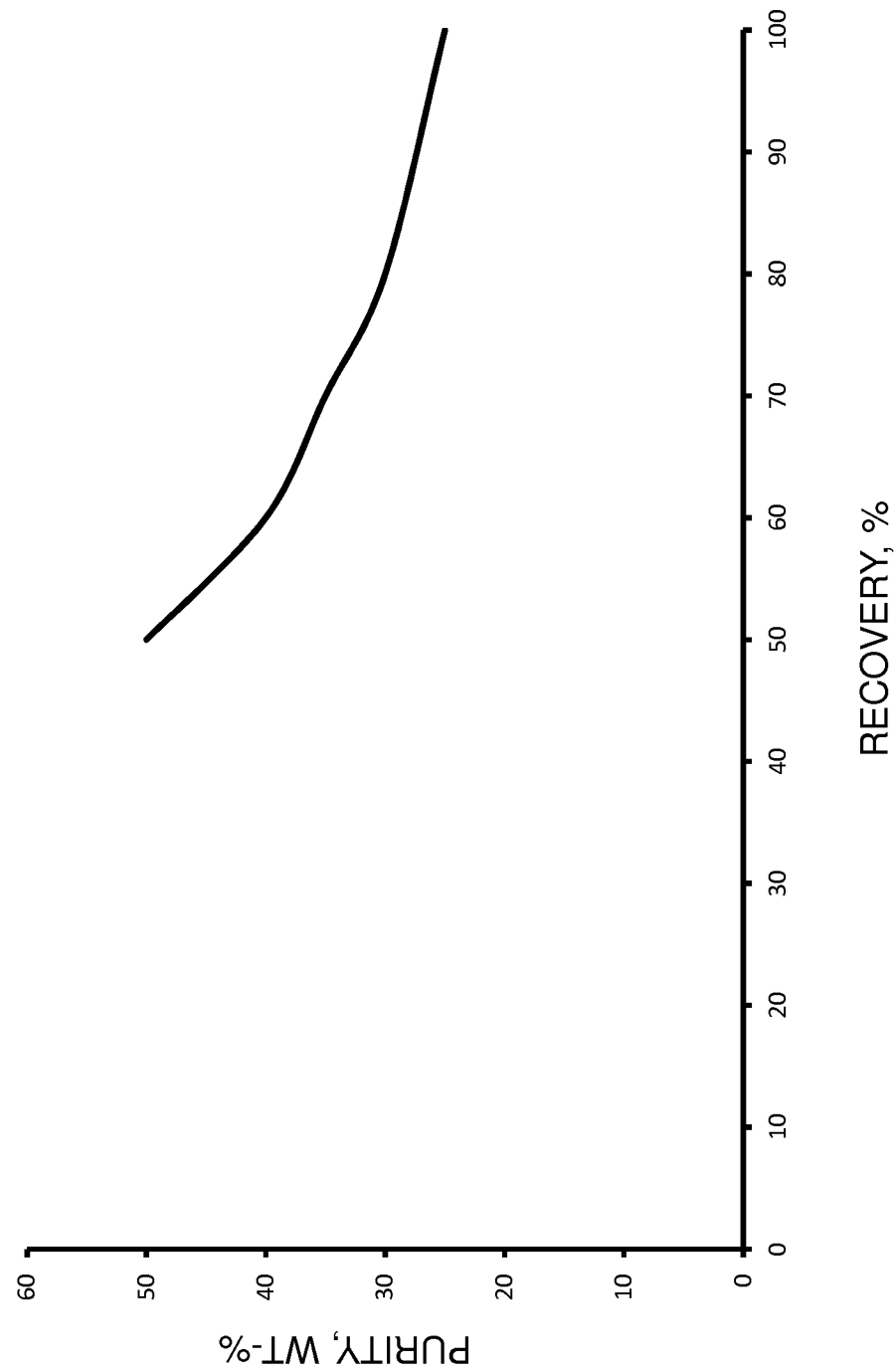
FIG. 9 is a chart showing the purity of the recovered astaxanthin as a function of the recovery of the astaxanthin on a weight basis for the separation of astaxanthin from neutral lipids.

The extraction of astaxanthin from a krill meal extract was carried out over steam activated carbon. A 50 gram quantity of steam activated carbon (having a particle size of about 40 by 70 μm) was packed in a 22 mm (ID, inside diameter) by 300 mm (Length) stainless steel column. A feed stream comprising 5 wt % dry mass of krill meal extract dissolved in a solvent mixture of 98:2 w/w ethanol to water was loaded onto the activated carbon by passing the feed stream through the column at a fed rate of 5 ml/minute at room temperature and atmospheric pressure while the color of the elute was monitored by UV-Vis spectrometry. The passing of the feed stream was continued for about 105 bed volumes (BV) until the color of the eluate was the same as the color of the feed stream as measured by UV-Vis Spectrometry. The passing of the feed stream was discontinued, and 7 bed volumes (about 800 ml) of heptane were passed through the column as a solvent to wash any lipids from the steam activated carbon. 3 Bed Volumes of Anisole (342 mL) were then passed through the column to remove the concentrated astaxanthin from the steam activated carbon adsorbent and collected. FIG. 9 shows the purity (wt-%) of the astaxanthin recovered as function of the recovery (weight %) of the astaxanthin. The purity of the astaxanthin ranged from about 50 wt-% to about 100 wt-% as the recovery of the astaxanthin ranged from about 50 wt-% to about 25 wt-%

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

We claim:

1. A process for continuous desalting of a krill oil extract stream to provide a desalted lipid rich stream, said process comprising:
    a) diluting the krill oil extract stream comprising polar lipids, neutral lipids, trimethylamine N-oxide, salts, and astaxanthin to a desalter concentration of about 2 and about 7 wt-% on a dry basis in a polar solvent comprising ethanol and water having an ethanol:water ratio of between of about 95:5 to 99:1 to provide a diluted krill oil stream;
    b) continuously passing the diluted krill oil stream to a filtration zone having a 0.45 micron filter to provide a filtered desalter feed stream;
    c) continuously passing the filtered desalter feed stream to a desalting zone having a plurality of desalting stages comprising at least two active desalting stages undergoing a desalting process, and at least one regenerating desalting stage undergoing a regeneration cycle, each active desalting stage and each regenerating desalting stage comprising a cation column containing a cation adsorbent in serial fluid communication with an anion column containing an anion adsorbent to adsorb the salt and the trimethylamine N-oxide, each cation column and each anion column having a top and a bottom, the desalting process comprising:
        i. distributing the filtered desalter feed stream to the at least two active desalting stages, one active desalting stage being in a lead position and one active being in a terminal position and operating in parallel such that a portion of the filtered desalter feed stream is passed to the top of each cation column and a portion of a desalted effluent stream is withdrawn from the bottom of each anion column of each of the at least two active desalting stages and collecting the portion of the desalted effluent stream from the active desalting stages to provide a first desalted krill oil stream comprising neutral lipids, polar lipids, and astaxanthin, and being substantially free of salt and trimethylamine N-oxide;
        ii. regenerating the regenerating desalting stage wherein the cation column is a regen cation column and wherein the anion column is a regen anion column according to the regeneration cycle comprising:
            (a) flushing the regenerating desalting stage with a mobile phase solvent having a ratio of 95:5 parts ethanol to water to a ratio of 99:1 parts ethanol to water to recover desalted lipids in a second desalted krill oil stream comprising neutral lipids, polar lipids, and astaxanthin, and being substantially free of salt and trimethylamine N-oxide;
            (b) washing the regenerating desalting stage with a water wash stream comprising water to provide a first waste stream;
            (c) reactivating the regen cation column by passing an acid stream comprising an aqueous hydrochloric acid solution comprising about 2 to about a 6 wt-% hydrochloric acid to the regen cation column to provide a reactivated regen cation column and withdrawing a second waste stream;
            (d) reactivating the regen anion column by passing an aqueous basic solution comprising about 5 to about 8 wt-% sodium carbonate to the regen anion column to provide a reactivated regen anion column and withdrawing a third waste stream;
            (e) separately washing the regen cation column and regen anion column with a water wash stream comprising water to remove excess ions and to provide a washed reactivated desalting stage and withdrawing a fourth waste stream; and,
            (f) passing the mobile phase solvent having a ratio of 95:5 parts ethanol to water to a ratio of 99:1 parts ethanol to water to recondition the reactivated desalting stage to provide a newly regenerated desalting stage;
    d) cycling the desalting zone by intermittently terminating distributing the filtered desalter feed stream to the active desalting stages and shifting or exchanging the newly regenerated desalting stage for the active desalting stage in the lead position and shifting the active desalting in the terminal position to become the regenerating desalting stage and to provide the process for continuous desalting of the krill oil extract stream; and,
    e) admixing the first desalted krill oil stream and the second desalted krill oil stream to provide the desalted lipid rich stream being substantially free of salt and trimethylamine N-oxide.

2. The process of claim 1, wherein the krill oil extract stream is selected from the group consisting of krill meal extract, krill oil wet paste and a krill oil product derived from solvent extraction of krill meal with ethanol to remove proteins and free carbohydrates.

3. The process of claim 1, wherein the first desalted krill oil stream comprises less than about 5 ppm of trimethylamine N-oxide or salt by weight on a dry basis.

4. The process of claim 1, wherein the cation adsorbent comprises a strong acid cation resin.

5. The process of claim 1, wherein the anion adsorbent comprises a weak base anion resin.

6. The process of claim 1, wherein the polar solvent comprises a mixture of ethanol and water having an ethanol to water ratio of 98:2.

7. The process of claim 1, wherein the krill oil extract stream is diluted to a concentration of about 5 wt-% on a dry basis.

8. The process of claim 1, wherein the desalted lipid rich stream comprises less than about 1 ppm of trimethylamine N-oxide or salt by weight on a dry basis.

9. The process of claim 1, wherein the desalting zone is a krill oil simulated moving bed desalting zone comprising 3 active desalting stages and 1 desalting stage undergoing desalting regeneration.

10. The process of claim 1, further comprising passing at least a portion of the desalted lipid rich stream to a first solvent recovery zone to remove the polar solvent in a first solvent stream and to provide a desalted krill oil product stream comprising neutral lipids, polar lipids and astaxanthin and being essentially free of trimethylamine N-oxide and salt.

11. The process of claim 10, further comprising passing at least a portion of the desalted lipid rich stream comprising neutral lipids, polar lipids, astaxanthin and polar solvent to an extraction zone to provide a polar lipid extract stream comprising solvent and polar lipids and being essentially free of neutral lipids and astaxanthin, and to provide a neutral lipid raffinate stream comprising solvent, neutral lipids and astaxanthin.

12. The process of claim 11, further comprising passing the neutral lipid raffinate stream to an astaxanthin separation zone to provide a second raffinate stream comprising neutral lipids and solvent and to provide an astaxanthin product stream.

13. The process of claim 11, further comprising admixing a portion of the desalted lipid rich stream and the polar lipid extract stream to provide at least one refined polar lipid product having a polar lipid content between about 40 and 99 wt-% polar lipids on a solvent free basis.

* * * * *